United States Patent
Xie et al.

(10) Patent No.: US 9,637,801 B2
(45) Date of Patent: May 2, 2017

(54) GEXP DETECTION KITS FOR IDENTIFICATION OF 11 KINDS OF DUCK VIRUS DISEASES

(71) Applicant: Guangxi Veterinary Research Institute, Guangxi (CN)

(72) Inventors: Zhixun Xie, Guangxi (CN); Yanfang Zhang, Guangxi (CN); Liji Xie, Guangxi (CN); Jiabo Liu, Guangxi (CN); Qing Fan, Guangxi (CN); Sisi Luo, Guangxi (CN); Xianwen Deng, Guangxi (CN); Zhiqin Xie, Guangxi (CN); Yaoshan Pang, Guangxi (CN)

(73) Assignee: Guangxi Veterinary Research Institute, Guangxi (CN)

( * ) Notice: Subject to any disclaimer, the term of this patent is extended or adjusted under 35 U.S.C. 154(b) by 0 days.

(21) Appl. No.: 14/787,319

(22) PCT Filed: Mar. 21, 2014

(86) PCT No.: PCT/CN2014/000313
§ 371 (c)(1),
(2) Date: Oct. 27, 2015

(87) PCT Pub. No.: WO2015/109427
PCT Pub. Date: Jul. 30, 2015

(65) Prior Publication Data
US 2016/0060716 A1    Mar. 3, 2016

(30) Foreign Application Priority Data

Jan. 26, 2014  (CN) .............................. 201410037453

(51) Int. Cl.
*C12Q 1/70* (2006.01)

(52) U.S. Cl.
CPC ....... *C12Q 1/701* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

FOREIGN PATENT DOCUMENTS

| CN | 102899424 A | 1/2013 |
| CN | 103320540 A | 9/2013 |
| CN | 103382507 A | 11/2013 |
| CN | 103468827 A | 12/2013 |

OTHER PUBLICATIONS

GenBank Accession No. AY962259.3; Nov. 16, 2006; [online] available at <http://www.ncbi.nlm.nih.gov/nuccore/118076404?report=genbank>; Retrieved on Jul. 25, 2016.*
GenBank Accession No. EF449516.1; Apr. 20, 2010; [online] available at <http://www.ncbi.nlm.nih.gov/nuccore/ef449516>; Retrieved on Aug. 16, 2016.*
Tang et al. A multiplex RT-PCR assay for detection and differentiation of avian H3, H5, and H9 subtype influenza viruses and Newcastle disease viruses. J Virol Methods 2012; 181: 164-169.*
Yang et al. Genotyping of 11 human papillomaviruses by multiplex PCR with a GeXP analyzer. J Med Virol 2012; 84: 957-963.*
Li et al. Comparative analysis of the genes UL1 through UL7 of the duck enteritis virus and other herpesviruses of the subfamily Alphaherpesvirinae. Genet Mol Biol 2009, 32: 121-128.*
Plummer et al. Detection of duck enteritis virus by polymerase chain reaction. Avian Dis 1998; 42: 554-564.*
Xie et al., "A multiplex RT-PCR for detection of type A influenza virus and differentiation of avian H5, H7, and H9 hemagglutinin subtypes", Molecular and Cellular Probes, 2006, pp. 245-249, vol. 20.
Luo et al., "Development of GeXP Assay for Simultaneous Differentiation of Six Chicken Respiratory Viruses", Chinese Journal of Virology, May 2013, pp. 250-257, vol. 29, No. 3.
Tingting et al., "Isolation and Identification of Duck Tembusu Virus from Guangxi", Chinese Journal of Animal Health Inspection, 2013, pp. 31-35, vol. 30, No. 6.
Xie et al., "Newcastle Disease Oil-emulsion Vaccines Prepared with Vegetable Oil", Chinese Journal of Preventive Veterinary Medicine, Jul. 2000, pp. 262-266, vol. 22, No. 4.
Zhang et al., "Development of a duplex RT-PCR assay for detection of duck tembusu virus and duck plague virus", Journal of Southern Agriculture, 2014, pp. 314-317, vol. 45, No. 2.
Huang et al., "Study on pathogenicity of Muscovy duck flower liver disease", Chinese Journal of Veterinary Science and Technology, 2003, pp. 7-9, vol. 33, No. 5.
Huang et al., "Isolation and Identification of Guangxi Muscovy Duck Parvovirus", Guangxi Journal of Animal Husbandry and Veterinary Medicine, 2002, pp. 5-7, vol. 18, No. 6.
Qu et al., "Investigation on Infection of Duck Circovirus in Part Regions of Guangxi Province", Chinese Animal Husbandry and Veterinary Medicine, 2010, pp. 156-158, vol. 37, No. 11.

* cited by examiner

*Primary Examiner* — Angela M Bertagna
(74) *Attorney, Agent, or Firm* — The Webb Law Firm (57) ABSTRACT

Provided herein is a GeXP detection kit for identification of 11 kinds of duck virus diseases. The detection kit includes a primer set for identifying or auxiliarily identifying pathogens of duck communicable diseases, including one or more of primer pair A, primer pair B primer pair C, primer pair D, primer pair E, primer pair F, primer pair G, primer pair H, primer pair I, primer pair J, primer pair K and primer pair L. The kit can detect simultaneously avian influenza virus, subtype H5, H7 and H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus with the primer set, PCR reagent or primer pairs provided in the present invention.

14 Claims, 2 Drawing Sheets

```
                       SEQUENCE LISTING

<160> NUMBER OF SEQ ID NOS: 24

<210> SEQ ID NO 1
<211> LENGTH: 37
<212> TYPE: DNA
<213> ORGANISM: Artificial Sequence
<220> FEATURE:
<223> OTHER INFORMATION: primer

<400> SEQUENCE: 1
aggtgacact atagaataca gaaacggatg ggagtgc                            37

<210> SEQ ID NO 2
<211> LENGTH: 43
<212> TYPE: DNA
<213> ORGANISM: Artificial Sequence
<220> FEATURE:
<223> OTHER INFORMATION: primer

<400> SEQUENCE: 2
gtacgactca ctatagggat atcaagtgca agatcccaat gat                    43

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
aggtgacact atagaatact tcaggcatca aaatgcaca                         39

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
gtacgactca ctatagggat agtttgttca tttctgagtc ggtc                   44
```

```
<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
aggtgacact atagaataaa tggggchttc atagctcc                              38

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
gtacgactca ctatagggat gatagcartc rccttcacaa                            40

<210> SEQ ID NO 7
<211> LENGTH: 41
<212> TYPE: DNA
<213> ORGANISM: Artificial Sequence
<220> FEATURE:
<223> OTHER INFORMATION: primer

<400> SEQUENCE: 7
aggtgacact atagaataac aacaagtgtg acaacagaag a                          41

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
gtacgactca ctatagggat cttccgtggc tctctcc                               37

<210> SEQ ID NO 9
<211> LENGTH: 41
<212> TYPE: DNA
<213> ORGANISM: Artificial Sequence
<220> FEATURE:
<223> OTHER INFORMATION: primer

<400> SEQUENCE: 9
aggtgacact atagaatatc ttcgttgtga aacggattac c                          41

<210> SEQ ID NO 10
<211> LENGTH: 43
<212> TYPE: DNA
<213> ORGANISM: Artificial Sequence
<220> FEATURE:
<223> OTHER INFORMATION: primer

<400> SEQUENCE: 10
gtacgactca ctatagggat gcctggacag atdtgtgcct act                        43

<210> SEQ ID NO 11
<211> LENGTH: 36
<212> TYPE: DNA
<213> ORGANISM: Artificial Sequence
<220> FEATURE:
<223> OTHER INFORMATION: primer
```

```
<400> SEQUENCE: 11
aggtgacact atagaatagg gaggagcaaa caaaga                                36

<210> SEQ ID NO 12
<211> LENGTH: 39
<212> TYPE: DNA
<213> ORGANISM: Artificial Sequence
<220> FEATURE:
<223> OTHER INFORMATION: primer

<400> SEQUENCE: 12
gtacgactca ctatagggaa tcgcaaattc catcacata                             39

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
aggtgacact atagaataat ggacagggtc atcagcgg                              38

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
gtacgactca ctatagggag aatrgctccy gccaatgct                             39

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
aggtgacact atagaatagt rgcagcaagr acaagg                                36

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
gtacgactca ctatagggac atatcygcat acatcaa                               37

<210> SEQ ID NO 17
<211> LENGTH: 38
<212> TYPE: DNA
<213> ORGANISM: Artificial Sequence
<220> FEATURE:
<223> OTHER INFORMATION: primer

<400> SEQUENCE: 17
aggtgacact atagaataaa tcggcaactc aagacatc                              38

<210> SEQ ID NO 18
<211> LENGTH: 39
```

<212> TYPE: DNA
<213> ORGANISM: Artificial Sequence
<220> FEATURE:
<223> OTHER INFORMATION: primer

<400> SEQUENCE: 18
gtacgactca ctatagggac ccattcataa acaggattc                        39

<210> SEQ ID NO 19
<211> LENGTH: 39
<212> TYPE: DNA
<213> ORGANISM: Artificial Sequence
<220> FEATURE:
<223> OTHER INFORMATION: primer

<400> SEQUENCE: 19
aggtgacact atagaataca gttgagccgg ayggtaatt                        39

<210> SEQ ID NO 20
<211> LENGTH: 45
<212> TYPE: DNA
<213> ORGANISM: Artificial Sequence
<220> FEATURE:
<223> OTHER INFORMATION: primer

<400> SEQUENCE: 20
gtacgactca ctatagggaa ctcggttggt gttagtvgcv tagaa                 45

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
aggtgacact atagaatact ttcaggctac atcttcaa                         38

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
gtacgactca ctatagggaa attctctttt cacccatcc                        39

<210> SEQ ID NO 23
<211> LENGTH: 38
<212> TYPE: DNA
<213> ORGANISM: Artificial Sequence
<220> FEATURE:
<223> OTHER INFORMATION: primer

<400> SEQUENCE: 23
aggtgacact atagaatatg ckccaaagag tcgacata                         38

```
<210> SEQ ID NO 24
<211> LENGTH: 41
<212> TYPE: DNA
<213> ORGANISM: Artificial Sequence
<220> FEATURE:
<223> OTHER INFORMATION: primer

<400> SEQUENCE: 24
gtacgactca ctatagggac aaaygcataa cggctctttc c                          41
```

GEXP DETECTION KITS FOR IDENTIFICATION OF 11 KINDS OF DUCK VIRUS DISEASES

CROSS REFERENCE TO RELATED APPLICATIONS

This application is the United States national phase of international Application No. PCT/CN2014/000313 filed Mar. 21, 2014, and claims priority to Chinese Patent Application No. 201410037453.1 filed Jan. 26, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1510356_ST25.txt. The size of the text file is 4,628 bytes, and the text file was created on Oct. 26, 2015.

FIELD OF THE INVENTION

The present invention relates to Biotechnology field, in particular relates to GeXP detection kits for identification of 11 kinds of duck virus diseases.

BACKGROUND OF THE INVENTION

Subtypes H5, H7 and H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus are 11 kinds of major communicable diseases severely harm to duck. With the development of duck breeding, the incidence of duck communicable virus diseases is also gradually increasing, which has become an important factor which restricts the development of duck breeding. Traditional methods of differential diagnosing these duck communicable diseases mainly include isolation and identification of pathogen, serological tests etc., while these methods are often limited by freshness of clinical samples, pollution degree of clinical samples, or course of disease of clinical samples, the operations thereof are also very complicated, time-consuming, furthermore, it is more difficult for these methods to differential diagnose multiplex infections. In recent years, with the development of molecular biology, PCR technology has been widely used in detection of duck communicable diseases, and multiplex PCR detection technology has been established, which can detect several kinds of pathogens at the same time and needs several primer pairs to be mixed together and amplify competitively and simultaneously, while the interference will emerge between these primers, with addition of each primer pair, the sensitivity decreases. PCR products need to be observed by agarose gel electrophoresis which is difficult to distinguish bands within 50 bp-100 bp, and generally only duplex-sextuple PCRs can be carried out, so it is difficult to achieve high throughput detection. Multiplex fluorescent PCR generally can only detect quadruplex PCR, because probes need to be labeled with fluorescent groups with different light emitting wavelengths, if probes labeled with too many fluorescent groups, interference will emerge between each other, so multiplex fluorescent PCR can only detect duplex-quadruplex PCR. Because several primer pairs are present in the multiplex PCR reaction system at the same time, the possibility of forming complex primer dimers greatly increases, and target gene number which can be detected simultaneously is limited (usually 2-6 genes), all these reasons cause that the multiplex PCR cannot achieve the goal of high throughput and rapid detection and analysis.

GeXP system (Gene Expression Profiler Genetic Analysis System) is a platform developed by Beckman Coulter Company in the USA and used to study the quantitative analysis of multi-gene expression, GeXP system consisting of 2 parts: GeXP eXpression Profiler software used to design primers and capillary electrophoresis of GenomeLab™ GeXP Genetic Analysis System used to analyze results, of which the latter can well separate the adjacent amplification fragments with gaps of more than 7 bps. GeXP multiplex PCR amplification combines universal primers labeled with fluorescence markers and specific chimeric primers (namely sequences with 5' ends of gene specific primers connecting to the universal primers) to cause the amplification of multiplex systems. At the beginning of the PCR reaction, reverse transcription reaction proceeds with the combination of reverse specific chimeric primer and original template, then the second chain of cDNA is synthetized by forward specific chimeric primer, after that, the specific sequences of forward and reverse chimeric primers initiate PCR reaction with cDNA as the template, complementary sequences of universal primers are respectively amplified; then universal primers labeled by fluorescence markers and dominated in the reaction system combine with complementary sequences thereof, causing subsequent amplification, and universal primers are complementary to base sequences labeled with fluorescence markers in the reaction system, PCR products are separated by GeXP capillary electrophoresis, and PCR products labeled with fluorescence markers are detected by GeXP detection window, then the lengths of the amplification fragments are calculated based on migration time of test fragments and standard molecular fragments (DNA Size Standard, DSS), the fluorescence signal intensity reflects the amplification content of the separated fragments. GeXP system can effectively analyze up to 40 target genes in the same system.

The key of establishing a detection method and making a detection kit for simultaneous identification of multiple pathogens with GeXP Multiplex Genes Expression Profiler Genetic Analysis System is to design specific primers and combine multiplex primers, then to use universal primers and convert the amplification of multiplex primers to the amplification of 1 pair of universal primer, so as to achieve the goal of high throughput detection. At present, there is no reagent or detection kit which can simultaneously detect multiple pathogens of communicable diseases from duck source based on GeXP system.

SUMMARY OF THE INVENTION

One of the purposes of the present invention is to provide a GeXP detection primer set for identifying or auxiliarily identifying pathogens of duck communicable diseases.

A GeXP detection primer set provided by the invention for identifying or auxiliarily identifying pathogens of duck communicable diseases consists of primer pair A, primer pair B primer pair C, primer pair D, primer pair E, primer pair F, primer pair G, primer pair H, primer pair I, primer pair J, primer pair K and primer pair L, wherein all primer pairs can be used alone;

said primer pair A consists of a single-stranded DNA shown as SEQ ID NO: 1 and a single-stranded DNA shown as SEQ ID NO: 2;

said primer pair B consists of a single-stranded DNA shown as SEQ ID NO: 3 and a single-stranded DNA shown as SEQ ID NO: 4;

said primer pair C consists of a single-stranded DNA shown as SEQ ID NO: 5 and a single-stranded DNA shown as SEQ ID NO: 6;

said primer pair D consists of a single-stranded DNA shown as SEQ ID NO: 7 and a single-stranded DNA shown as SEQ ID NO: 8;

said primer pair E consists of a single-stranded DNA shown as SEQ ID NO: 9 and a single-stranded DNA shown as SEQ ID NO: 10;

said primer pair F consists of a single-stranded DNA shown as SEQ ID NO: 11 and a single-stranded DNA shown as SEQ ID NO: 12;

said primer pair G consists of a single-stranded DNA shown as SEQ ID NO: 13 and a single-stranded DNA shown as SEQ ID NO: 14;

said primer pair H consists of a single-stranded DNA shown as SEQ ID NO: 15 and a single-stranded DNA shown as SEQ ID NO: 16;

said primer pair I consists of a single-stranded DNA shown as SEQ ID NO: 17 and a single-stranded DNA shown as SEQ ID NO: 18;

said primer pair J consists of a single-stranded DNA shown as SEQ ID NO: 19 and a single-stranded DNA shown as SEQ ID NO: 20;

said primer pair K consists of a single-stranded DNA shown as SEQ ID NO: 21 and a single-stranded DNA shown as SEQ ID NO: 22;

said primer pair L consists of a single-stranded DNA shown as SEQ ID NO: 23 and a single-stranded DNA shown as SEQ ID NO: 24.

In the above primer set, every primer of the primer pairs A, B, C, D, E, F, G, H, I, J, K and L is mixed with each other equimolarly;

said pathogens of duck communicable diseases are subtype H5 of avian influenza virus, subtype H7 of avian influenza virus, subtype H9 of avian influenza virus, duck hepatitis virus, duck enteritis virus, duck Tembusu virus, Newcastle disease virus, egg drop syndrome virus, Muscovy duck reovirus, Muscovy duck parvovirus and/or duck circovirus.

Another purpose of the present invention is to provide a GeXP detection PCR reagent for identifying or auxiliarily identifying pathogens of duck communicable diseases.

The GeXP detection PCR reagent provided in the present invention comprises the above primer set.

The above PCR reagent consists of PCR amplification buffer, primer pairs A-L of the above primer set, MgCl$_2$, DNA polymerase and water;

the concentration of every primer of said primer pairs A-L in said PCR reagent is 10 nM.

In the above PCR reagent, said pathogens of duck communicable diseases are subtype H5 of avian influenza virus, subtype H7 of avian influenza virus, subtype H9 of avian influenza virus, duck hepatitis virus, duck enteritis virus, duck Tembusu virus, Newcastle disease virus, egg drop syndrome virus, Muscovy duck reovirus, Muscovy duck parvovirus and/or duck circovirus.

The third purpose of the present invention is to provide a GeXP detection kit for identifying or auxiliarily identifying pathogens of duck communicable diseases.

The detection kit provided in the invention comprises the above primer set or the above PCR reagent.

In the above detection kit, said pathogens of duck communicable diseases are subtype H5 of avian influenza virus, subtype H7 of avian influenza virus, subtype H9 of avian influenza virus, duck hepatitis virus, duck enteritis virus, duck Tembusu virus, Newcastle disease virus, egg drop syndrome virus, Muscovy duck reovirus, Muscovy duck parvovirus and/or duck circovirus.

The protection scope of the present invention also includes a use of the above primer set or the above PCR reagent or the above detection kit in the preparation of products detecting or auxiliarily detecting with the GeXP whether a test sample carries pathogens of duck communicable diseases.

In the above use, said pathogens of duck communicable diseases are subtype H5 of avian influenza virus, subtype H7 of avian influenza virus, subtype H9 of avian influenza virus, duck hepatitis virus, duck enteritis virus, duck Tembusu virus, Newcastle disease virus, egg drop syndrome virus, Muscovy duck reovirus, Muscovy duck parvovirus and/or duck circovirus.

Types of pathogens which are detectable for the primer pairs of the reagents or the detection kits provided in the present invention are respectively as follows: the primer pair A can detect 16 types of subtype HA of avian influenza virus, namely subtypes H1-H16 of avian influenza virus; the primer pair B can detect subtype H5 of avian influenza virus; the primer pair C can detect subtype H7 of avian influenza virus; the primer pair D can detect subtype H9 of avian influenza virus; the primer pair E can detect duck hepatitis virus; the primer pair F can detect duck enteritis virus; the primer pair G can detect duck Tembusu virus; the primer pair H can detect Newcastle disease virus; the primer pair I can detect egg drop syndrome virus; the primer pair J can detect Muscovy duck reovirus; the primer pair K can detect Muscovy duck parvovirus; the primer pair L can detect duck circovirus.

Avian source can specifically be chicken source or duck source, but is not limited to the above sources of the above virus.

The experiments in the present invention prove that it has a high specificity to detect simultaneously avian influenza virus, subtypes H5, H7 and H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus with the 12 prime pairs of reagent or detection kit based on GeXP system provided in the present invention, and the sensitivity thereof is respectively 10 copies/µL, 100 copies/µL, 100 copies/µL, 100 copies/µL, 10 copies/µL, 100 copies/µL, 10 copies/µL, 10 copies/µL, 100 copies/µL, 10 copies/µL, 100 copies/µL, 100 copies/µL, and compared with identification results with conventional experimental methods, such as virus isolation and hemagglutination inhibition test etc., the coincidence rate reaches 100%. The invention provides a simple, high-throughput detection kit and detection system for common and major duck communicable diseases and pathogens thereof, meeting with actual needs better and having a broad prospect of application.

DESCRIPTION OF DRAWINGS

FIGS. 1-3: Horizontal coordinate represents base number of amplification products and vertical coordinate represents the fluorescence signal value.

DETAILED DESCRIPTION OF THE INVENTION

If there is no special instruction, experimental methods used in the following examples are conventional methods.

If there is no special instruction, materials and reagents used in the following examples can be obtained from a commercial way.

Some materials and reagents used in the following examples are as follows:

Avian influenza virus strains: Duck/HK/717/79-d1 (subtype H1N3), Duck/HK/77/76 (subtype H2N3), Duck/HK/526/79/2B (subtype H3N6), Duck/HK/668/79 (subtype H4N5), Duck/HK/531/79 (subtype H6N8), Turkey/ont/6118/68 (subtype H8N4), Duck/Guangxi/1/00 (subtype H9N2), Duck/HK/876/80 (subtype H10N3), Duck/HK/661/79 (subtype H11N3), Duck/HK/862/80 (subtype H12N5), Gull/MD/704/77 (subtype H13N5) are all recorded in "Zhixun Xie, Yao-shan Pang, Jiabo Liu, et al. A multiplex RT-PCR for detection of type A influenza virus and differentiation of avian H5, H7, and H9 hemagglutinin subtypes", Molecular and Cellular Probes, 2006, 20(3-4): 245-249, the public can obtain from the Guangxi Veterinary Research Institute.

Avian influenza virus strains Duck/HK/313/78 (subtype H5N3) and Duck/HK/47/76 (subtype H7N2) are both recorded in "Establishment of GeXP detection method for simultaneous identification of 6 types of chicken viral respiratory diseases", Chinese Journal of Virology, 2013, 2 (3): 250-257, and are provided by the University of Hong Kong, the public can obtain from the Guangxi Veterinary Research Institute; these two samples are preserved in the form of cDNA and have been confirmed by HA gene sequencing.

Duck hepatitis virus strain AV2111 is purchased from China Institute of Veterinary Drugs Control;

Duck enteritis virus strain AV1221 is purchased from China Institute of Veterinary Drugs Control;

Duck Tembusu virus is recorded in "Isolation and Identification of 4 Strains of Duck Tembusu Virus from Guangxi", Chinese Journal of Animal Health Inspection, 2013, 30 (6): 31-35, the public can obtain from the Guangxi Veterinary Research Institute;

Newcastle disease virus is recorded in "Research on Vegetable Oil Emulsion Vaccine of Newcastle Disease Virus", Chinese Journal of Preventive Veterinary Medicine, 2000, (04): 23-27, the public can obtain from the Guangxi Veterinary Research Institute;

Egg drop syndrome virus is recorded in "Establishment of duplex RT-PCR Detection Method for Duck Tembusu Virus and Duck enteritis virus", Journal of Southern Agriculture, 2014, 45 (2): 314-317, the public can obtain from the Guangxi Veterinary Research Institute;

Muscovy duck reovirus is recorded in "Research on Pathogen of Muscovy Duck Flower Liver Disease", Chinese Journal of veterinary science and technology, 2003, 33 (5): 7-9, the public can obtain from the Guangxi Veterinary Research Institute;

Muscovy duck parvovirus is recorded in "Isolation and Identification of Guangxi Muscovy Duck Parvovirus", Guangxi Journal of Animal Husbandry and Veterinary Medicine, 2002, 18 (6): 5-7, the public can obtain from the Guangxi Veterinary Research Institute;

Duck circovirus is recorded in "Investigation on Infection of Duck Circovirus in Part Regions of Guangxi Province", Chinese animal husbandry and veterinary medicine, 2010, 37 (11): 156-158, the public can obtain from the Guangxi Veterinary Research Institute;

Example 1

Design of Primer Pairs

Primer sequences published by GenBank were taken as references, and the known sequences were downloaded from the NCBI and contrasted with each other with DNASTAR software, then highly conserved and specific gene fragments in each target gene were chosen and accordingly 12 specific primer pairs were designed by primer premier 5.0 software, and GeXP universal primers (underlined sequence) were added to 5' ends of primers, and the primer direction was all from 5' end to 3' end, specifically as follows:

1) Primer pair A taking gene M of avian influenza virus (AIV) as target gene:

```
AIV-F:
                                    (SEQ ID NO: 1)
AGGTGACACTATAGAATACAGAAACGGATGGGAGTGC;

AIV-R:
                                    (SEQ ID NO: 2)
GTACGACTCACTATAGGGATATCAAGTGCAAGATCCCAATGAT;
```

The expected length of the amplification product (namely the position of target peak) was 122 bps;

2) Primer pair B taking gene HA of subtype H5 of avian influenza virus (AIV-H5) as target gene:

```
AIV-H5-F:
                                    (SEQ ID NO: 3)
AGGTGACACTATAGAATACTTCAGGCATCAAAATGCACA;

AIV-H5-R:
                                    (SEQ ID NO: 4)
GTACGACTCACTATAGGGATAGTTTGTTCATTTCTGAGTCGGTC;
```

The expected length of the amplification product (namely the position of target peak) was 286 bps;

3) Primer pair C taking gene HA of subtype H7 of avian influenza virus (AIV-H7) as target gene:

```
AIV-H7-F:
                                    (SEQ ID NO: 5)
AGGTGACACTATAGAATAAATGGGGCHTTCATAGCTCC;

AIV-H7-R:
GTACGACTCACTATAGGGATGATAGCARTCRCCTTCACAA (SEQ ID NO: 6, wherein R was a degenerate base,representing A or G);
```

The expected length of the amplification product (namely the position of target peak) was 144 bps;

4) Primer pair D taking gene HA of subtype H9 of avian influenza virus (AIV-H9) as target gene:

```
AIV-H9-F:
                                       (SEQ ID NO: 7)
AGGTGACACTATAGAATAACAACAAGTGTGACAACAGAAGA;

AIV-H9-R:
                                       (SEQ ID NO: 8)
GTACGACTCACTATAGGGATCTTCCGTGGCTCTCTCC;
```

The expected length of the amplification product (namely the position of target peak) was 237 bps;

5) Primer pair E taking region 5' UTR of duck hepatitis virus (DHV) as target gene:

```
DHV-F:
                                       (SEQ ID NO: 9)
AGGTGACACTATAGAATATCTTCGTTGTGAAACGGATTACC;

DHV-R:
GTACGACTCACTATAGGGATGCCTGGACAGATDTGTGCCTACT (SEQ ID NO: 10, wherein D was a degenerate gene, representing A or G or T);
```

The expected length of the amplification product (namely the position of target peak) was 133 bps;

6) Primer pair F taking gene UL6 of duck enteritis virus (DEV) as target gene:

```
DEV-F:
                                       (SEQ ID NO: 11)
AGGTGACACTATAGAATAGGGAGGAGCAAACAAAGA;

DEV-R:
                                       (SEQ ID NO: 12)
GTACGACTCACTATAGGGAATCGCAAATTCCATCACATA;
```

The expected length of the amplification product (namely the position of target peak) was 151 bps;

7) Primer pair G taking gene E of duck Tembusu virus (DTMUV) as target gene:

```
DTMUV-F:
                                       (SEQ ID NO: 13)
AGGTGACACTATAGAATAATGGACAGGGTCATCAGCGG;

DTMUV-R:
GTACGACTCACTATAGGGAGAATRGCTCCYGCCAATGCT (SEQ ID NO: 14, wherein R was a degenerate gene, representing A or G; Y was a degenerate gene, representing C or T);
```

The expected length of the amplification product (namely the position of target peak) is 177 bps;

8) Primer pair H taking gene L of Newcastle disease virus (NDV) as target gene:

```
NDV-F:
AGGTGACACTATAGAATAGTRGCAGCAAGRACAAGG (SEQ ID NO: 15, wherein R was a degenerate gene, representing A or G)
```

```
NDV-R:
GTACGACTCACTATAGGGACATATCYGCATACATCAA (SEQ ID NO: 16, wherein Y was a degenerate gene, representing C or T)
```

The expected length of the amplification product (namely the position of target peak) was 196 bps;

9) Primer pair I taking gene penton of egg drop syndrome virus (EDSV) as target gene:

```
EDSV-F:
                                       (SEQ ID NO: 17)
AGGTGACACTATAGAATAAATCGGCAACTCAAGACATC;

EDSV-R:
                                       (SEQ ID NO: 18)
GTACGACTCACTATAGGGACCCATTCATAAACAGGATTC;
```

The expected length of the amplification product (namely the position of target peak) was 208 bps;

10) Primer pair J taking gene S1 of Muscovy duck reovirus (MDRV) as target gene:

```
MDRV-F:
AGGTGACACTATAGAATACAGTTGAGCCGGAYGGTAATT (SEQ ID NO: 19, wherein Y was a degenerate gene, representing C or T)

MDRV-R:
GTACGACTCACTATAGGGAACTCGGTTGGTGTTAGTVGCVTAGAA (SEQ ID NO: 20, wherein V was a degenerate gene, representing A or G or C);
```

The expected length of the amplification product (namely the position of target peak) was 218 bps;

11) Primer pair K taking gene VP1 of Muscovy duck parvovirus (MDPV) as target gene:

```
MDPV-F:
                                       (SEQ ID NO: 21)
AGGTGACACTATAGAATACTTTCAGGCTACATCTTCAA;

MDPV-R:
                                       (SEQ ID NO: 22)
GTACGACTCACTATAGGGAAATTCTCTTTTCACCCATCC;
```

The expected length of the amplification product (namely the position of target peak) was 253 bps;

12) Primer pair L taking gene REP of duck circovirus (DuCV) as target gene:

```
DuCV-F:
AGGTGACACTATAGAATATGCKCCAAAGAGTCGACATA (SEQ ID NO: 23, wherein K was a degenerate gene, representing T or G);

DuCV-R:
GTACGACTCACTATAGGGACAAAYGCATAACGGCTCTTTCC (SEQ ID NO: 24, wherein Y was a degenerate gene, representing C or T);
```

The expected length of the amplification product (namely the position of target peak) was 300 bps;

Because of differences of pathogen strains in the actual detection and deviation of GeXP system, such as capillary electrophoresis of GenomeLab™ GeXP Genetic Analysis System, the actual lengths of detected amplification products obtained with the above primer pairs A-L and GeXP universal primer pair can fluctuate up and down for 3 bps around the expected length of the amplification products.

Example 2

Detection for the Specificity of Primer Pairs

I. Preparation of templates
1. Extraction of virus RNA and acquisition of cDNA
1) Extraction of virus RNA With DNA/RNA Extraction Kit (purchased from TransGen Biotech Co. Ltd., catalog number is ER201), according to kit instructions, RNA of the following virus was extracted respectively (with samples obtained from duck embryo allantoic fluid which were negative for the following virus as negative control samples): avian influenza virus strains: Duck/HK/717/79-d1 (subtype H1N3), Duck/HK/77/76 (subtype H2N3), Duck/HK/526/79/2B (subtype H3N6), Duck/HK/668/79 (subtype H4N5), Duck/HK/531/79 (subtype H6N8), Turkey/ont/6118/68 (subtype H8N4), Duck/Guangxi/1/00 (subtype H9N2), Duck/HK/876/80 (subtype H10N3), Duck/HK/661/79 (subtype H11N3), Duck/HK/862/80 (subtype H12N5), Gull/MD/704/77, (subtype H13N5); duck hepatitis virus, duck Tembusu virus, Newcastle disease virus, Muscovy duck reovirus.

2) Acquisition of cDNA

The RNA samples obtained in step 1) proceeded with reverse transcription respectively in accordance with the following reaction system and reaction conditions, then the cDNA was obtained; DEPC water served as a control of total RNA.

Reaction system (20 μL): 5× Reverse Transcriptase Buffer 4 μL, Random Primer (9mer) 50 pmol, dNTP Mixture (10 mM) 2 μL, Ribonuclease Inhibitor 20 U, AMV Reverse Transcriptase, Template RNA 1 μg, and DEPC water was added to the reaction system to make it up to 20 μL.

Reverse transcription reagent Random Primer (9mer), dNTP Mixture, Ribonuclease Inhibitor, Reverse Transcriptase XL (AMV) (all purchased from Dalian TaKaRa Company, catalog numbers were respectively D3802, D4030RA, D2313A, D2620).

Reaction conditions: the extracted total RNA to which DEPC water and Random Primer (9mer) had been added proceeded with short spin, then was kept at 70° C. for 10 min, after that the extracted total RNA was immediately kept in ice bath for 5 min. Then after addition of the remaining four substances, short spin was proceeded, 42° C. 1.5 h, preserved at −20° C.

3) Avian influenza virus strain Duck/HK/313/78 (subtype H5N3) and Duck/HK/47/76 (subtype H7N2) were respectively preserved in the form of cDNA and had been confirmed by HA gene sequencing.

2. Extraction of genomic DNA

With DNA/RNA Extraction Kit (all purchased from TransGen Biotech Co. Ltd., catalog number is ER201), according to kit instructions, virus genomic DNA of egg drop syndrome virus, duck enteritis virus, duck circovirus and Muscovy duck parvovirus was extracted respectively (with samples obtained from duck embryo allantoic fluid which were negative for these virus as negative control samples).

3. Determination of nucleic acid content

OD value was determined with nucleic acid and protein analyzer BioPhotometer, then the value of concentration and purity was obtained to control the quality of nucleic acid.

II. Detection for the Specificity of Primer Pairs for Single PCR

1. Detection for the specificity of primer pair A
1) PCR amplification cDNA samples of 13 subtypes HA of avian influenza disease strains, duck hepatitis virus, duck Tembusu virus, Newcastle disease virus and Muscovy duck reovirus obtained in step 1 of step I and DNA samples of egg drop syndrome virus, duck enteritis virus, duck circovirus and Muscovy duck parvovirus obtained in step 2 of step I were amplified by PCR respectively with primer pair A, said 13 subtypes HA of avian influenza disease were Duck/HK/717/79-d1 (subtype H1N3), Duck/HK/77/76 (subtype H2N3), Duck/HK/526/79/2B (subtype H3N6), Duck/HK/668/79 (subtype H4N5), Duck/HK/531/79 (subtype H6N8), Turkey/ont/6118/68 (subtype H8N4), Duck/Guangxi/1/00 (subtype H9N2), Duck/HK/876/80 (subtype H10N3), Duck/HK/661/79 (subtype H11N3), Duck/HK/862/80 (subtype H12N5), Gull/MD/704/77, (subtype H13N5), Duck/HK/313/78 (subtype H5N3) and Duck/HK/47/76 (subtype H7N2), with cDNA samples and DNA samples obtained in step system and program were as follows:

Reaction system (20 μL): GenomeLab™ GeXP Start Kit 5×PCR Buffer (comprising GeXP universal primer pair, Beckman company, US, PN A85017) 4 μL, primer pair A (the final concentration of each primer in the reaction system was 10 nM), 25 mM $MgCl_2$ 4 μL (Beckman company, US, PN A25395), JumpStart Taq DNA polymerase 1.4 μL (sigma company, US, D4184), template cDNA or DNA 0.5 pg-0.5 μg, and sterile water was added to the reaction system to make it up to 20 μL. Each cDNA/DNA reaction system was set to 3 repetitions.

Reaction program: 95° C. 30 s, 55° C. 30 s, 72° C. 30 s, 10 cycles; 95° C. 30 s, 63° C. 30 s, 72° C. 30 s, 10 cycles; 95° C. 30 s, 50° C. 30 s, 72° C. 30 s, 20 cycles; 4° C. end.

2) Capillary electrophoresis

PCR products obtained in step 1) were detected simultaneously by capillary electrophoresis with GenomeLab GeXP Genetic Analysis System, the operation steps were as follows: using formamide as loading buffer (Beckman Coulter company, US, catalog number 608082), mixing completely DNA size standard Kit-400 Base Pairs (Beckman Coulter company, US, catalog number 608098) with loading buffer at the volume ratio of 1:(80-160), adding 39 μL mixed liquid into each well of sample plate, diluting PCR products 10-100 folds, adding 1 μL diluted PCR products into sample plate and blending, finally dropping a drop of paraffin oil in each well to seal, in order to avoid formamide oxidation and sample evaporation. Adding buffer into each well of buffer plate in ⅔ and proceeding capillary electrophoresis. The conditions of capillary electrophoresis were as follows: heating of capillary: temperature 50° C.; denaturation: 90° C., 120 s; sample injection: 2.0 KV, 30 s; separation: 6.0 KV, 35 min. Analyzing detected results with GenomeLab GeXP Genetic Analysis System.

Results: cDNA samples of 13 subtypes HA of avian influenza virus strains can be amplified to obtain amplification products of 120 bps-123 bps, and confirmed by sequencing that the lengths of amplification products of 13 subtypes were all 122 bps, the sequences of the amplification products were target sequences of primer pair A; non-avian influenza virus and the negative controls had no amplification product. The results shows that the specificity of the primer pair A is high, which can specifically detect 13 subtypes HA of avian influenza virus (subtypes H1-H13). In addition, sequences of primer pair A have a high identity with RNA sequences of subtypes H14, H15 and H16 of avian influenza virus, which can be showed in the comparison of NCBI BLAST, for instance, the sequences of primer pair A have a 100.00% identity with target primer sequences of H14N6 (accession number: CY005394), H14N5 (accession number: CY014605), H14N5 (accession number: GU052253), H15N9 (accession number: CY077617), H15N9 (accession number: GU052261), H15N9 (accession number: CY005406), H16N3 (accession number: HM060055), that means primer pair A can also detect subtypes H14, H15 and H16 of avian influenza virus.

2. Detection for the specificity of primer pair B

1) PCR amplification cDNA samples of subtype H5 (H5N3) of avian influenza disease strains obtained in step 1 of step I were amplified by PCR with primer pair B, simultaneously cDNA samples of subtypes H7N2 and H9N2 of avian influenza disease strains, duck hepatitis virus, duck Tembusu virus, Newcastle disease virus and Muscovy duck reovirus obtained in step 1 of step I and DNA samples of egg drop syndrome virus, duck enteritis virus, duck circovirus and Muscovy duck parvovirus obtained in step 2 of step I were also amplified by PCR respectively with primer pair B, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of subtype H5 of avian influenza virus strains can be amplified to obtain amplification products of 285 bps-287 bps, and confirmed by sequencing that the length of amplification products of H5N3 subtypes was 286 bps, the sequences of the amplification products were target sequences of primer pair B; non-H5 subtype of avian influenza virus and the negative controls had no amplification product. The results show that the specificity of the primer pair B is high, which can specifically detect subtype H5 of avian influenza virus.

3. Detection for the specificity of primer pair C

1) PCR amplification cDNA samples of subtype H7 (H7N2) of avian influenza disease strains obtained in step 1 of step I were amplified by PCR with primer pair C, simultaneously cDNA samples of subtypes H5N3 and H9N2 of avian influenza disease strains, duck hepatitis virus, duck Tembusu virus, Newcastle disease virus and Muscovy duck reovirus obtained in step I and DNA samples of egg drop syndrome virus, duck enteritis virus, duck circovirus and Muscovy duck parvovirus obtained in step 2 of step I were also amplified by PCR respectively with primer pair C, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of subtype H7 of avian influenza virus strains can be amplified to obtain amplification products of 142 bps-145 bps, and confirmed by sequencing that the length of amplification products of subtype H7N2 was 144 bps, the sequences of the amplification products were target sequences of primer pair C; non-H7 subtype of avian influenza virus and the negative controls had no amplification product. The results show that the specificity of the primer pair C is high, which can specifically detect H7 subtype of avian influenza virus.

4. Detection for the specificity of primer pair D

1) PCR amplification cDNA samples of subtype H9 (H9N2) of avian influenza virus strains obtained in step 1 of step I were amplified by PCR with primer pair D, simultaneously cDNA samples of subtypes H5N3 and H7N2 of avian influenza disease strains, duck hepatitis virus, duck Tembusu virus, Newcastle disease virus and Muscovy duck reovirus obtained in step I and DNA samples of egg drop syndrome virus, duck enteritis virus, duck circovirus and Muscovy duck parvovirus obtained in step 2 of step I were also amplified by PCR respectively with primer pair D, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of subtype H9 of avian influenza virus strains can be amplified to obtain amplification products of 223 bps-239 bps, and confirmed by sequencing that the length of amplification products of H9N2 subtypes was 237 bps, the sequences of the amplification products were target sequences of primer pair D; non-H9 subtype of avian influenza virus and the negative controls had no amplification product. The results show that the specificity of the primer pair D is high, which can specifically detect H9 subtype of avian influenza virus.

5. Detection for the specificity of primer pair E

1) PCR amplification cDNA samples of duck hepatitis virus obtained in step 1 of step I were amplified by PCR with primer pair E, simultaneously cDNA samples of subtypes H5 (H5N3), H7N2 and H9N2 of avian influenza disease strains, duck Tembusu virus, Newcastle disease virus and Muscovy duck reovirus obtained in step I and DNA samples of egg drop syndrome virus, duck enteritis virus, duck circovirus and Muscovy duck parvovirus obtained in step 2 of step I were also amplified by PCR respectively with primer pair E, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of duck hepatitis virus can be amplified to obtain amplification products of 132 bps-135 bps, and confirmed by sequencing that the length of amplification products of duck hepatitis virus was 133 bps, the sequences of the amplification products were target sequences of primer pair E; non-duck hepatitis virus and the negative controls had no amplification product. The results show that the specificity of the primer pair E is high, which can specifically detect duck hepatitis virus.

6. Detection for the specificity of primer pair F

1) PCR amplification

DNA samples of duck enteritis virus obtained in step 2 of step I were amplified by PCR with primer pair F, simultaneously cDNA samples of subtypes H5N3, H7N2 and H9N2 of avian influenza disease strains, duck hepatitis virus, duck Tembusu virus, Newcastle disease virus and Muscovy duck reovirus obtained in step I and DNA samples of egg drop syndrome virus, duck circovirus and Muscovy duck parvovirus obtained in step 2 of step I were also amplified by PCR respectively with primer pair F, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: DNA samples of duck enteritis virus can be amplified to obtain amplification products of 150 bps-15 3 bps, and confirmed by sequencing that the length of amplification products of duck enteritis virus was 151 bps, the sequences of the amplification products were target sequences of primer pair F; non-duck enteritis virus and the negative controls had no amplification product. The results show that the specificity of the primer pair F is high, which can specifically detect duck enteritis virus.

7. Detection for the specificity of primer pair G

1) PCR amplification cDNA samples of duck Tembusu virus obtained in step 1 of step I were amplified by PCR with primer pair G, simultaneously cDNA samples of subtypes H5N3, H7N2 and H9N2 of avian influenza disease strains, duck hepatitis virus, Newcastle disease virus and Muscovy duck reovirus obtained in step I and DNA samples of egg drop syndrome virus, duck enteritis virus, duck circovirus and Muscovy duck parvovirus obtained in step 2 of step I were also amplified by PCR respectively with primer pair G, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of duck Tembusu virus can be amplified to obtain amplification products of 175 bps-178 bps, and confirmed by sequencing that the length of amplification products of duck Tembusu virus was 176 bps, the sequences of the amplification products were target sequences of primer pair G; non-duck Tembusu virus and the negative controls had no amplification product. The results show that the specificity of the primer pair G is high, which can specifically detect duck Tembusu virus.

8. Detection for the specificity of primer pair H

1) PCR amplification cDNA samples of Newcastle disease virus obtained in step 1 of step I were amplified by PCR with primer pair H, simultaneously cDNA samples of subtypes H5N3, H7N2 and H9N2 of avian influenza disease strains, duck hepatitis virus, duck Tembusu virus and Muscovy duck reovirus obtained in step I and DNA samples of egg drop syndrome virus, duck enteritis virus, duck circovirus and Muscovy duck parvovirus obtained in step 2 of step I were also amplified by PCR respectively with primer pair H, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of Newcastle disease virus can be amplified to obtain amplification products of 195 bps-198 bps, and confirmed by sequencing that the length of amplification products of Newcastle disease virus was 196 bps, the sequences of the amplification products were target sequences of primer pair H; non-Newcastle disease virus and the negative controls had no amplification product. The results show that the specificity of the primer pair H is high, which can specifically detect Newcastle disease virus.

9. Detection for the specificity of primer pair I

1) PCR amplification

DNA samples of egg drop syndrome virus obtained in step 2 of step I were amplified by PCR with primer pair I, simultaneously cDNA samples of subtypes H5N3, H7N2 and H9N2 of avian influenza disease strains, duck hepatitis virus, duck Tembusu virus, Newcastle disease virus and Muscovy duck reovirus obtained in step I and DNA samples of duck enteritis virus, duck circovirus and Muscovy duck parvovirus obtained in step 2 of step I were also amplified by PCR respectively with primer pair I, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: DNA samples of egg drop syndrome virus can be amplified to obtain amplification products of 207 bps-210 bps, and confirmed by sequencing that the length of amplification products of egg drop syndrome virus was 208 bps, the sequences of the amplification products were target sequences of primer pair I; non-egg drop syndrome virus and the negative controls had no amplification product. The results show that the specificity of the primer pair I is high, which can specifically detect egg drop syndrome virus.

10. Detection for the specificity of primer pair J

1) PCR amplification cDNA samples of Muscovy duck reovirus obtained in step 1 of step I were amplified by PCR with primer pair J, simultaneously cDNA samples of subtypes H5N3, H7N2 and H9N2 of avian influenza disease strains, duck hepatitis virus, duck Tembusu virus, Newcastle disease virus obtained in step I and DNA samples of egg drop syndrome virus, duck enteritis virus, duck circovirus and Muscovy duck parvovirus obtained in step 2 of step I were also amplified by PCR respectively with primer pair J, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: cDNA samples of Muscovy duck reovirus can be amplified to obtain amplification products of 218 bps-221 bps, and confirmed by sequencing that the length of amplification products of Muscovy duck reovirus was 218 bps, the sequences of the amplification products were target sequences of primer pair J; non-Muscovy duck reovirus and the negative controls had no amplification product. The results show that the specificity of the primer pair J is high, which can specifically detect Muscovy duck reovirus.

12. Detection for the specificity of primer pair K

1) PCR amplification

DNA samples of Muscovy duck parvovirus obtained in step 2 of step I were amplified by PCR with primer pair K, simultaneously cDNA samples of subtypes H5N3, H7N2 and H9N2 of avian influenza disease strains, duck hepatitis virus, duck Tembusu virus, Newcastle disease virus and Muscovy duck reovirus obtained in step I and DNA samples of egg drop syndrome virus, duck enteritis virus and duck circovirus obtained in step 2 of step I were also amplified by PCR respectively with primer pair K, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: DNA samples of Muscovy duck parvovirus can be amplified to obtain amplification products of 252 bps-255 bps, and confirmed by sequencing that the length of amplification products of Muscovy duck parvovirus was 253 bps, the sequences of the amplification products were target sequences for primer pair K; non-Muscovy duck parvovirus and the negative controls had no amplification product. The results show that the specificity of the primer pair K is high, which can specifically detect Muscovy duck parvovirus.

12. Detection for the specificity of primer pair L

1) PCR amplification

DNA samples of duck circovirus obtained in step 2 of step I were amplified by PCR with primer pair L, simultaneously cDNA samples of subtypes H5N3, H7N2 and H9N2 of avian influenza disease strains, duck hepatitis virus, duck Tembusu virus, Newcastle disease virus and Muscovy duck reovirus obtained in step I and DNA samples of egg drop syndrome virus, duck enteritis virus and Muscovy duck parvovirus obtained in step 2 of step I were also amplified by PCR respectively with primer pair L, and with cDNA samples and DNA samples obtained in step I from duck embryo allantoic fluid which were negative for these virus as negative control, reaction system and program were the same as those used in the part of detection for specificity of primer pair A.

2) Capillary electrophoresis

The method was in the same way as that used in the part of detection for specificity of primer pair A.

Results: DNA samples of duck circovirus can be amplified to obtain amplification products of 299 bps-302 bps, and confirmed by sequencing that the length of amplification products of duck circovirus was 300 bps, the sequences of the amplification products were target sequences for primer pair L; non-duck circovirus and the negative controls had no amplification product. The results show that the specificity of the primer pair L is high, which can specifically detect duck circovirus.

III. Detection for the Specificity of the Mixture of 12 Primer Pairs 1) primer pairs A, B, C, D, E, F, G, H, I, J, K and L were added to one PCR reaction system, cDNA samples of 1 subtype H5 of avian influenza disease strain, 1 subtype H7 of avian influenza disease strain, 1 subtype H9 of avian influenza disease strain, duck hepatitis virus, duck Tembusu virus, Newcastle disease virus and Muscovy duck reovirus obtained in step I and cDNA or DNA samples of egg drop syndrome virus, duck enteritis virus, duck circovirus and Muscovy duck parvovirus obtained in step 2 of step I were amplified respectively by PCR, with cDNA samples and DNA samples obtained in step I from duck embryo allantoic fluid which were negative for these virus as negative control, reaction system and program were as follows:

Reaction system (20 µL): GenomeLab™ GeXP Start Kit 5×PCR Buffer (comprising GeXP universal primer pair, Beckman company, US, PN A85017) 4 µL, primer pairs A, B, C, D, E, F, G, H, I, J, K and L (the final concentration of each primer of each primer pair in the reaction system was 10 nM), 25 mM $MgCl_2$ 4 µL (Beckman company, US, PN A25395); JumpStart Taq DNA polymerase 1.4 µL (sigma company, US, D4184); template cDNA or DNA 0.5 pg-0.5 µg; sterile water was added to the reaction system to make it up to 20 µL. Each cDNA/DNA was set to 3 repetitions.

Reaction program: 95° C. 30 s, 55° C. 30 s, 72° C. 30 s, 10 cycles; 95° C. 30 s, 63° C. 30 s, 72° C. 30 s, 10 cycles; 95° C. 30 s, 50° C. 30 s, 72° C. 30 s, 20 cycles; 4° C. end.

2) Capillary electrophoresis: the method was in the same way as that used in the part of detection for specificity of primer pair A.

Results: single cDNA or DNA sample of 11 kinds of pathogens (subtypes H5, H7 and H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus) was detected respectively with the mixture of 12 primer pairs of A-L, as a result, amplification products of 122 bps and 286 bps, 122 bps and 144 bps, 122 bps and 237 bps, 133 bps, 150 bps, 176 bps, 196 bps, 208 bps, 218 bps, 253 bps and 300 bps were detected, and the negative control had no amplification product.

The above results show that: the mixing of primer pairs A-L does not have any influence on the specificity of detection of each primer pair and can be used for specific detection of each kind of pathogens of avian influenza virus, subtypes H5, H7 and H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus.

Therefore, primer pairs A-L, PCR reagents comprising the primer pairs A-L or PCR kit comprising primer pairs A-L can all be used for GeXP detection of test samples, so as to determine whether the test sample contains avian influenza virus, subtypes H5, H7 and H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus;

PCR reagent of each 20 µL consists of 5×PCR Buffer, primer pairs A-L, 25 mM $MgCl_2$ (the final concentration was 5 mM/µL) 4 µL, Tag DNA polymerase 1.4 µL (the final concentration was 0.175 unit/µL), template cDNA or DNA, and the rest are sterile water.

Determine whether the test sample contains the corresponding virus by the following judgments:

if the amplification products of prime pair A are within 120-123 bps and the amplification products of primer pair B are within 285-287 bps, the test sample contains the subtype H5 of avian influenza virus;

if the amplification products of prime pair A are within 120-123 bps and the amplification products of primer pair C are within 142-145 bps, the test sample contains the subtype H7 of avian influenza virus;

if the amplification products of prime pair A are within 120-123 bps and the amplification products of primer pair D are within 236-239 bps, the test sample contains the subtype H9 of avian influenza virus;

if the amplification products of prime pair E are within 132-135 bps, the test sample contains duck hepatitis virus;

if the amplification products of prime pair F are within 150-153 bps, the test sample contains duck enteritis virus;

if the amplification products of prime pair G are within 175-178 bps, the test samples contains duck Tembusu virus;

if the amplification products of prime pair H are within 195-198 bps, the test samples contains Newcastle disease virus;

if the amplification products of prime pair I are within 207-210 bps, the test samples contains egg drop syndrome virus;

if the amplification products of prime pair J are within 218-221 bps, the test samples contains Muscovy duck reovirus;

if the amplification products of prime pair K are within 252-255 bps, the test samples contains Muscovy duck parvovirus;

if the amplification products of prime pair L are within 299-302 bps, the test samples contains duck circovirus.

Example 3

Detection for the Sensitivity of Primer Pairs

I. Preparation of Monoclonal Plasmid Standard and Subtype H7 of Avian Influenza Virus Both Containing Target Gene With cDNA or DNA samples of subtype H5 of Avian influenza virus Duck/HK/313/78 (subtype H5N3), subtype H7 of Avian influenza virus Duck/HK/47/76 (subtype H7N2), subtype H9 of Avian influenza virus Duck/Guangxi/1/00 (subtype H9N2), duck hepatitis virus, duck enteritis virus, duck Tembusu virus, Newcastle disease virus, egg drop syndrome virus, Muscovy duck reovirus, Muscovy duck parvovirus and duck circovirus as templates, full-sized cDNAs or DNA fragments of gene M of avian influenza virus, gene HA of subtype H5 of avian influenza virus, gene HA of subtype H7 of avian influenza virus, gene HA of subtype H9 of avian influenza virus, gene of region 5' UTR of duck hepatitis virus, gene UL6 of duck enteritis virus, gene E of duck Tembusu virus, gene L of Newcastle disease virus, gene penton of egg drop syndrome virus, gene S1 of Muscovy duck reovirus, gene VP1 of Muscovy duck parvovirus and gene REP of duck circovirus were obtained by PCR amplifying, then the full-sized cDNAs or the DNA fragments were connected with plasmids pMD 18-T vector (purchased from TAKARA Clontech) respectively so as to obtain 12 kinds of recombinant plasmids PA, PB, PC, PD, PE, PF, PG, PH, PI, PJ, PK and PL, and confirmed by sequencing that these 12 kinds of recombinant plasmids were the ones respectively inserting one kind of the above genes into plasmid pMD 18-T vector, and can be taken as the target genes of 12 primer pairs of A-L.

The concentration of each recombinant plasmid containing target gene was measured with UV spectrophotometer and according to the molecular weight and concentrations of the recombinant plasmids the corresponding copy numbers were calculated. Each recombinant plasmid of high concentration was diluted as a single plasmid dilution in which concentration of target gene was $10^6$, $10^5$, $10^4$, $10^3$, $10^2$, or $10^1$ copies/μL. All kinds of recombinant plasmids were mixed to prepare a mixed solution in which concentration of each kind of plasmid was $10^5$ copies/μL, then the mixed solution was diluted as the ones in which concentration of each kind of plasmid was $10^4$, $10^3$, $10^2$ copies/μL.

II. Detection for the Sensitivity of the Mixture of 12 Primer Pairs

1. With the mixture of primer pairs A-L as primers and with different single plasmid dilutions of different concentrations as templates, PCR amplification and capillary electrophoresis were carried out with the method used in step III of Example 2; as a result, the sensitivity of detection for avian influenza virus is 10 copies/μL, the sensitivity of detection for subtype H5 of avian influenza virus is 10 copies/μL, the sensitivity of detection for subtype H7 of avian influenza virus is 100 copies/μL, the sensitivity of detection for subtype H9 of avian influenza virus is 100 copies/μL, the sensitivity of detection for duck hepatitis virus is 10 copies/μL, the sensitivity of detection for duck enteritis virus is 100 copies/μL, the sensitivity of detection for duck Tembusu virus is 10 copies/μL, the sensitivity of detection for Newcastle disease virus is 10 copies/μL, the sensitivity of detection for egg drop syndrome virus is 10 copies/μL, the sensitivity of detection for Muscovy duck reovirus is 10 copies/μL, the sensitivity of detection for Muscovy duck parvovirus is 100 copies/μL, the sensitivity of detection for duck circovirus is 100 copies/μL.

2. With the mixture of primer pairs A-L as primers and mixed plasmid dilutions of 12 kinds of plasmid of different concentration as templates, PCR amplification and capillary electrophoresis were carried out with the method used in step III of Example 2; as a result, the sensitivity of detection for avian influenza virus is 10 copies/μL, the sensitivity of detection for subtype H5 of avian influenza virus is 100 copies/μL, the sensitivity of detection for subtype H7 of avian influenza virus is 100 copies/μL, the sensitivity of detection for subtype H9 of avian influenza virus is 100 copies/μL, the sensitivity of detection for duck hepatitis virus is 10 copies/μL, the sensitivity of detection for duck enteritis virus is 100 copies/μL, the sensitivity of detection for duck Tembusu virus is 10 copies/μL, the sensitivity of detection for Newcastle disease virus is 100 copies/μL, the sensitivity of detection for egg drop syndrome virus is 100 copies/μL, the sensitivity of detection for Muscovy duck reovirus is 10 copies/μL, the sensitivity of detection for Muscovy duck parvovirus is 100 copies/μL, the sensitivity of detection for duck circovirus is 100 copies/μL.

Example 4

The Accuracy of Detection with Primer Pairs

I. The Accuracy of Detection with the Mixture of 12 Primer Pairs cDNA samples of subtype H5 of avian influenza virus Duck/HK/313/78 (subtype H5N3) and subtype H7 of avian influenza virus Duck/HK/47/76 (H7N2 subtype) which were both identified by HA gene sequencing were sampled, subtype H9 of avian influenza virus Duck/Guangxi/1/00 (H9N2 type), duck hepatitis virus, duck enteritis virus, duck Tembusu virus, Newcastle disease virus, egg drop syndrome virus, Muscovy duck reovirus, Muscovy duck parvovirus and duck circovirus which were identified with common experimental methods, such as: virus isolation, hemagglutination inhibition test, neutralization test etc (cDNA or DNA were extracted with the method used in step I of Example 2) were sampled. cDNA or DNA samples of the above single pathogen, cDNA or DNA samples simulating clinical infection with the above pathogens, mixed template of cDNA or DNA samples of the above pathogens were respectively amplified with PCR and detected with electrophoresis, the specific results are as follows:

1. cDNA or DNA samples of 11 kinds of single virus can be detected for target peak of corresponding virus without any miscellaneous peaks, which are consistent with the detection results obtained with common experimental methods, such as sequencing, virus isolation, hemagglutination inhibition test, neutralization test etc.

2. Simulated clinical infection

Figure 1:
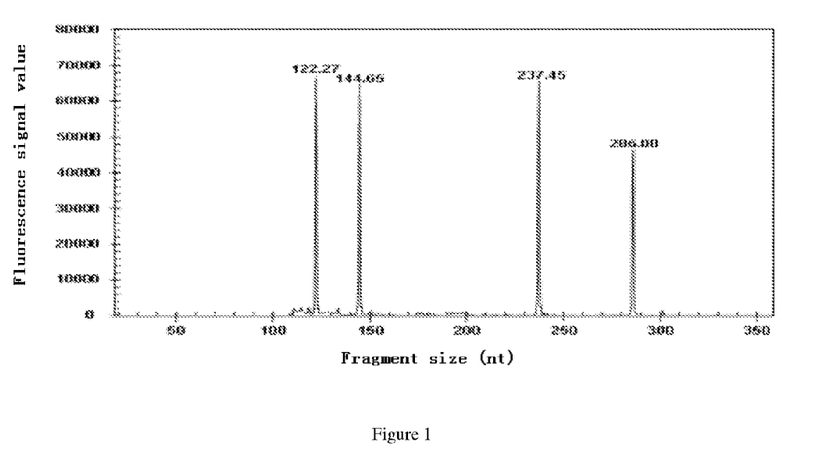
FIG. 1: Capillary electrophoresis analysis for GeXP 12-plex PCR with mixed cDNA templates of subtypes H5, H7, H9 of avian influenza virus.
Figure 2:
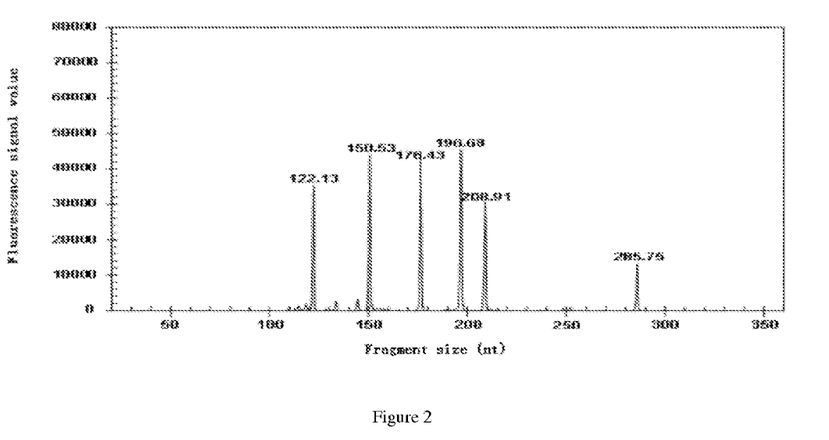
FIG. 2: Capillary electrophoresis analysis for GeXP 12-plex PCR with mixed cDNA templates of subtype H5 of avian influenza virus, duck Tembusu virus, egg drop syndrome virus, duck enteritis virus and Newcastle disease virus.

Several cDNAs or DNAs of the above 11 kinds of pathogens were selected randomly and mixed, and 2 experimental groups were as follows:

Group 1: cDNAs of subtype H5N3, subtype H7N2 and subtype H9N2 of avian influenza virus were mixed as templates, Group 2: DNA of duck enteritis virus, cDNA of duck Tembusu virus, cDNA of Newcastle disease virus, DNA of egg drop syndrome virus and cDNA of subtype H5N3 of avian influenza virus were mixed as templates;

As measured with the method used in the step III of Example 2, Group 1 detected 4 target peaks of 122.14 bps and 144.92 bps, 122.14 bps and 237.21 bps, 122.14 bps, 285.73 bps (see in FIG. 1), which shows that the sample contains the templates of subtypes H5, H9 and H7 of avian influenza virus, the result is in coincidence with the actual situation; Group 2 detected 5 target peaks of 122.13 bps and 285.75 bps, 150.53 bps, 176.43 bps, 196.68 bps, 208.91 bps without any miscellaneous peaks, which shows that the sample contains the templates of cDNA of subtype H5 of avian influenza virus, DNA of duck enteritis virus, cDNA of duck Tembusu virus, cDNA of Newcastle disease virus and DNA of egg drop syndrome virus, the result is in coincidence with the actual situation.

Figure 3:
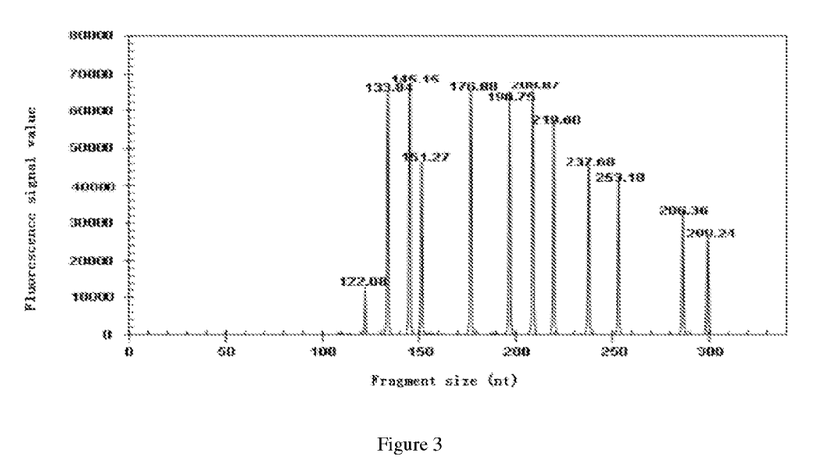
FIG. 3: Capillary electrophoresis analysis for GeXP 12-plex PCR of pathogens of 11 types of duck communicable diseases

3. Mixture of 11 kinds of pathogens 12 target peaks can be detected (FIG. 3) without any miscellaneous peaks, which shows that the samples contain cDNA or DNA templates of all pathogens of subtype H5 of avian influenza virus, subtype H7 of avian influenza virus, subtype H9 of avian influenza virus, duck hepatitis virus, duck enteritis virus, duck Tembusu virus, Newcastle disease virus, egg drop syndrome virus, Muscovy duck reovirus, Muscovy duck parvovirus and duck circovirus, the result is in coincidence with the actual situation.

The invention claimed is:

1. A gene expression profiler genetic analysis system (GeXP) detection primer set for identifying or auxiliarily identifying pathogens of duck communicable diseases, comprising primer pair J and one or more primer pairs selected from primer pair A, primer pair B, primer pair C, primer pair D, primer pair E, primer pair F, primer pair G, primer pair H, primer pair I, primer pair K and primer pair L, wherein:
said primer pair A consists of a single-stranded DNA of SEQ ID NO: 1 and a single-stranded DNA of SEQ ID NO: 2;
said primer pair B consists of a single-stranded DNA of SEQ ID NO: 3 and a single-stranded DNA of SEQ ID NO: 4;
said primer pair C consists of a single-stranded DNA of SEQ ID NO: 5 and a single-stranded DNA of SEQ ID NO: 6;
said primer pair D consists of a single-stranded DNA of SEQ ID NO: 7 and a single-stranded DNA of SEQ ID NO: 8;
said primer pair E consists of a single-stranded DNA of SEQ ID NO: 9 and a single-stranded DNA of SEQ ID NO: 10;
said primer pair F consists of a single-stranded DNA of SEQ ID NO: 11 and a single-stranded DNA of SEQ ID NO: 12;
said primer pair G consists of a single-stranded DNA of SEQ ID NO: 13 and a single-stranded DNA of SEQ ID NO: 14;
said primer pair H consists of a single-stranded DNA of SEQ ID NO: 15 and a single-stranded DNA of SEQ ID NO: 16;
said primer pair I consists of a single-stranded DNA of SEQ ID NO: 17 and a single-stranded DNA of SEQ ID NO: 18;
said primer pair J consists of a single-stranded DNA of SEQ ID NO: 19 and a single-stranded DNA of SEQ ID NO: 20;
said primer pair K consists of a single-stranded DNA of SEQ ID NO: 21 and a single-stranded DNA of SEQ ID NO: 22; and
said primer pair L consists of a single-stranded DNA of SEQ ID NO: 23 and a single-stranded DNA of SEQ ID NO: 24.

2. The primer set according to claim 1, wherein every primer of the primer pair J and the one or more of primer pairs chosen from primer pair A, primer pair B, primer pair C, primer pair D, primer pair E, primer pair F, primer pair G, primer pair H, primer pair I, primer pair K, and primer pair L is mixed with each other equimolarly; and
wherein said pathogens of duck communicable diseases are Muscovy duck reovirus and one or more of subtype H5 of avian influenza virus, subtype H7 of avian influenza virus, subtype H9 of avian influenza virus, duck hepatitis virus, duck enteritis virus, duck Tembusu virus, Newcastle disease virus, egg drop syndrome virus, Muscovy duck parovirus, and duck circovirus.

3. A GeXP detection kit for identifying or auxiliarily identifying pathogens of duck communicable diseases, comprising the primer set of claim 1 and one or more of a PCR amplification buffer, MgCl$_2$, a DNA polymerase, and water.

4. The GeXP detection kit according to claim 3, wherein: said GeXP detection kit includes a PCR reaction mixture of PCR amplification buffer, the primer set of claim 1, MgCl$_2$, DNA polymerase and water.

5. The GeXP detection kit according to claim 4, wherein: the concentration of each primer of said primer set in said PCR reaction mixture is 10 nM.

6. A method of detecting a communicable disease pathogen in a sample obtained from a duck, comprising:
conducting an amplification of pathogens in a sample obtained from a duck using primer pairs comprising primer pair J and one or more primer pairs chosen from primer pair A, primer pair B, primer pair C, primer pair D, primer pair E, primer pair F, primer pair G, primer pair H, primer pair I, primer pair K, and primer pair L, wherein:
said primer pair A consists of a single-stranded DNA of SEQ ID NO: 1 and a single-stranded DNA of SEQ ID NO: 2;
said primer pair B consists of a single-stranded DNA of SEQ ID NO: 3 and a single-stranded DNA of SEQ ID NO: 4;
said primer pair C consists of a single-stranded DNA of SEQ ID NO: 5 and a single-stranded DNA of SEQ ID NO: 6;
said primer pair D consists of a single-stranded DNA of SEQ ID NO: 7 and a single-stranded DNA of SEQ ID NO: 8;
said primer pair E consists of a single-stranded DNA of SEQ ID NO: 9 and a single-stranded DNA of SEQ ID NO: 10;
said primer pair F consists of a single-stranded DNA of SEQ ID NO: 11 and a single-stranded DNA of SEQ ID NO: 12;
said primer pair G consists of a single-stranded DNA of SEQ ID NO: 13 and a single-stranded DNA of SEQ ID NO: 14;
said primer pair H consists of a single-stranded DNA of SEQ ID NO: 15 and a single-stranded DNA of SEQ ID NO: 16;
said primer pair I consists of a single-stranded DNA of SEQ ID NO: 17 and a single-stranded DNA of SEQ ID NO: 18;
said primer pair J consists of a single-stranded DNA of SEQ ID NO: 19 and a single-stranded DNA of SEQ ID NO: 20;

said primer pair K consists of a single-stranded DNA of SEQ ID NO: 21 and a single-stranded DNA of SEQ ID NO: 22; and said primer pair L consists of a single-stranded DNA of SEQ ID NO: 23 and a single-stranded DNA of SEQ ID NO: 24.

7. The method according to claim 6, wherein:

the method detects Muscovy duck reovirus and subtype H5 of avian influenza virus and comprises using primer pairs J and B in the amplification reaction;

the method detects Muscovy duck reovirus and subtype H7 of avian influenza virus and comprises using primer pairs J and C in the amplification reaction; or the method detects Muscovy duck reovirus and subtype H9 of avian influenza virus and comprises using primer pairs J and D in the amplification reaction.

8. The method according to claim 6, wherein:

the method detects Muscovy duck reovirus and duck hepatitis virus and comprises using primer pairs J and E in the amplification reaction.

9. The method according to claim 6, wherein:

the method detects Muscovy duck reovirus and duck enteritis virus and comprises using primer pairs J and F in the amplification reaction.

10. The method according to claim 6, wherein:

the method detects Muscovy duck reovirus and duck Tembusu virus and comprises using primer pairs J and G in the amplification reaction.

11. The method according to claim 6, wherein:

the method detects Muscovy duck reovirus and Newcastle disease virus and comprises using primer pairs J and H in the amplification reaction.

12. The method according to claim 6, wherein:

the method detects Muscovy duck reovirus and egg drop syndrome virus and comprises using primer pairs J and I in the amplification reaction.

13. The method according to claim 6, wherein:

the method detects Muscovy duck reovirus and Muscovy duck parovirus and comprises using primer pairs J and K in the amplification reaction.

14. The method according to claim 6, wherein:

the method detects Muscovy duck reovirus and duck circovirus and comprises using primer pairs J and L in the amplification reaction.

* * * * *

UNITED STATES PATENT AND TRADEMARK OFFICE
CERTIFICATE OF CORRECTION

PATENT NO. : 9,637,801 B2  Page 1 of 1
APPLICATION NO. : 14/787319
DATED : May 2, 2017
INVENTOR(S) : Zhixun Xie et al.

It is certified that error appears in the above-identified patent and that said Letters Patent is hereby corrected as shown below:

In the Claims

Column 28, Line 15, Claim 2, delete "parovirus," and insert -- parvovirus, --

Column 30, Line 16, Claim 13, delete "parovirus" and insert -- parvovirus, --

Signed and Sealed this
Twentieth Day of June, 2017

Joseph Matal
*Performing the Functions and Duties of the
Under Secretary of Commerce for Intellectual Property and
Director of the United States Patent and Trademark Office*